US007531334B2

(12) United States Patent
Cheng et al.

(10) Patent No.: US 7,531,334 B2
(45) Date of Patent: May 12, 2009

(54) POLYMERIC MICROCARRIERS FOR CELL CULTURE FUNCTIONS

(75) Inventors: Chieh-Min Cheng, Rochester, NY (US); Mark A. Jackson, Rochester, NY (US)

(73) Assignee: Xerox Corporation, Norwalk, CT (US)

( * ) Notice: Subject to any disclaimer, the term of this patent is extended or adjusted under 35 U.S.C. 154(b) by 298 days.

(21) Appl. No.: 11/279,826

(22) Filed: Apr. 14, 2006

(65) Prior Publication Data
US 2007/0243607 A1 Oct. 18, 2007

(51) Int. Cl.
C12N 11/06 (2006.01)
C12N 11/08 (2006.01)
A61K 9/16 (2006.01)

(52) U.S. Cl. ............ 435/181; 435/180; 424/491; 424/497; 424/501; 428/402; 428/403

(58) Field of Classification Search ......... 435/181, 435/180; 424/491, 497, 501; 428/402, 403
See application file for complete search history.

(56) References Cited

U.S. PATENT DOCUMENTS

| 3,674,736 | A | | 7/1972 | Lerman et al. |
|---|---|---|---|---|
| 3,944,493 | A | | 3/1976 | Jadwin et al. |
| 4,007,293 | A | | 2/1977 | Mincer et al. |
| 4,079,014 | A | | 3/1978 | Burness et al. |
| 4,138,383 | A | | 2/1979 | Rembaum et al. |
| 4,243,694 | A | | 1/1981 | Mansukhani |
| 4,394,430 | A | | 7/1983 | Jadwin et al. |
| 4,438,239 | A | * | 3/1984 | Rembaum et al. ......... 525/54.1 |
| 4,444,961 | A | | 4/1984 | Timm |
| 4,560,635 | A | | 12/1985 | Hoffend et al. |
| 4,911,830 | A | | 3/1990 | Bromley et al. |
| 4,956,128 | A | | 9/1990 | Hommel et al. |
| 4,981,652 | A | | 1/1991 | Rhim et al. |
| 5,260,002 | A | | 11/1993 | Wang |
| 5,278,020 | A | | 1/1994 | Grushkin et al. |
| 5,290,654 | A | | 3/1994 | Sacripante et al. |
| 5,308,734 | A | | 5/1994 | Sacripante et al. |
| 5,344,738 | A | | 9/1994 | Kmiecik-Lawrynowicz et al. |
| 5,346,797 | A | | 9/1994 | Kmiecik-Lawrynowicz et al. |
| 5,348,832 | A | | 9/1994 | Sacripante et al. |
| 5,364,729 | A | | 11/1994 | Kmiecik-Lawrynowicz et al. |
| 5,366,841 | A | | 11/1994 | Patel et al. |
| 5,370,963 | A | | 12/1994 | Patel et al. |
| 5,370,964 | A | | 12/1994 | Patel et al. |
| 5,376,347 | A | | 12/1994 | Ipponmatsu et al. |
| 5,403,693 | A | | 4/1995 | Patel et al. |
| 5,405,728 | A | | 4/1995 | Hopper et al. |
| 5,418,108 | A | | 5/1995 | Kmiecik-Lawrynowicz et al. |
| 5,496,676 | A | | 3/1996 | Croucher et al. |
| 5,501,935 | A | | 3/1996 | Patel et al. |
| 5,527,658 | A | | 6/1996 | Hopper et al. |
| 5,554,480 | A | | 9/1996 | Patel et al. |
| 5,585,215 | A | | 12/1996 | Ong et al. |
| 5,593,807 | A | | 1/1997 | Sacripante et al. |
| 5,643,506 | A | | 7/1997 | Rourke |
| 5,650,255 | A | | 7/1997 | Ng et al. |
| 5,650,256 | A | | 7/1997 | Veregin et al. |
| 5,853,943 | A | | 12/1998 | Cheng et al. |
| 5,853,944 | A | | 12/1998 | Foucher et al. |
| 5,869,216 | A | | 2/1999 | Ong et al. |
| 5,902,710 | A | | 5/1999 | Ong et al. |
| 5,919,595 | A | | 7/1999 | Mychajlowskij et al. |
| 5,945,245 | A | | 8/1999 | Mychajlowskij et al. |
| 6,143,457 | A | | 11/2000 | Carlini et al. |
| 6,294,306 | B1 | * | 9/2001 | Kmiecik-Lawrynowicz et al. ............ 430/137.14 |
| 6,294,606 | B1 | | 9/2001 | Chen et al. |
| 6,348,561 | B1 | | 2/2002 | Mychajlowskij et al. |
| 6,458,565 | B1 | * | 10/2002 | Cunningham et al. ...... 435/70.3 |
| 6,780,558 | B2 | * | 8/2004 | Yamada et al. ........... 430/123.5 |
| 7,276,254 | B2 | * | 10/2007 | Burns et al. ............. 424/489 |
| 2004/0214247 | A1 | * | 10/2004 | De Kruif et al. ........... 435/7.23 |

OTHER PUBLICATIONS

Aksoy et al., "Stability of α-amylase immobilized on poly(methyl methacrylate-acrylic acid) microspheres," J Biotechnol 60:37-46, 1998.*
Malvern Instruments Ltd., Toner Industry Overview, http://www.malvern.co.uk/LabEng/industry/toners/overview.htm, printed from the Internet on Nov. 26, 2008.*
Exhibit A, size distribution of 25-micron diameter particles, one standard deviation equals 1/8 of the average diameter, prepared on Nov. 26, 2008.*
U.S. Appl. No. 10/063,656, filed May 7, 2002, Burns et al.
Amsden et al.; "An examination of factors affecting the size, distribution and release characteristics of polymer microbeads made using electrostatics"; Journal of Controlled Release; vol. 43; pp. 183-196; 1997.
Kamiyama et al.; "Micron-Sized Polymeric Microsphere by Suspension Polymerization"; Journal of Applied Polymer Science; vol. 50; pp. 107-113; 1993.
Leelarasamee et al.; "A method for the preparation of polylactic acid microcapsules of controlled particle size and drug loading"; J. Microencapsulation; vol. 5, No. 2; pp. 147-157; 1988.
O'Donnell et al.; "Properties of multiphase microspheres of poly(D,L-lactic-co-glycolic acid) prepared by a potentiometric dispersion technique"; J. Microencapsulation; vol. 12, No. 2; pp. 155-163; 1995.

(Continued)

*Primary Examiner*—Delia M. Ramirez
*Assistant Examiner*—Rosanne Kosson
(74) *Attorney, Agent, or Firm*—Oliff & Berridge, PLC

(57) ABSTRACT

Polymeric microcarriers suitable for use in cell culture processes and the methods of making such polymeric microcarriers by emulsion/aggregation polymerization processes.

22 Claims, No Drawings

OTHER PUBLICATIONS

Reyderman et al.; "Novel Methods of Microparticulate Production: Application to Drug Delivery"; Pharmaceutical Development and Technology; vol. 1(3); pp. 223-229; 1996.

Sansdrap et al.; "Influence of manufacturing parameters on the size characteristics and the release profiles of nifedipine from Poly(DL-lactide-co-glycolide) microspheres"; International Journal of Pharmaceutics; vol. 98; pp. 157-167; 1998.

Shiga et al.; "Preparation of Poly(D,L-lactide) and Copoly(lactide-glycolide) Microspheres of Uniform Size"; J. Pharm. Pharmacol.; vol. 48; pp. 891-895; 1996.

Sosnowski et al.; "Synthesis of Bioerodible Poly(e-caprolactone) Latexes and Poly(D,L-lactice) Microspheres by Ring-Opening Polymerization"; Journal of Bioactive and Compatible Polymers; vol. 9; pp. 345-366 ; 1994.

* cited by examiner

POLYMERIC MICROCARRIERS FOR CELL CULTURE FUNCTIONS

BACKGROUND

Disclosed herein are polymeric microcarriers suitable for culturing cells in a biologically active environment. The polymeric microcarriers have a small size of from about 20 microns to about 200 microns, such as from about 25 microns to about 175 microns or from about 35 microns to about 150 microns, and a narrow particle size distribution. Due to the small size of the polymeric microcarriers, many cells may be cultivated on each individual polymeric microcarriers. Also, disclosed herein are processes, for example, emulsion/aggregation polymerization processes, suitable for making the polymeric microcarriers described herein.

REFERENCES

Polymeric microcarriers, that is, microcarriers formed (at least in part) from polymer, have found a variety of uses in the research, medical and industrial areas.

Microcarriers, particularly polymeric microcarriers, also have found use in a wide range of other biological, medical and industrial uses. For example, microcarriers having a narrow size distribution have found uses in such areas as immunoassays, cell separation processes, cancer therapy, diagnostic testing and the like. In the biological and medical contexts, such polymeric microcarriers are finding increasing uses in both in vivo and in vitro applications. Likewise, polymeric microcarriers are finding increasing uses in laboratory testing, analysis and screening procedures.

Accordingly, there are numerous publications disclosing studies directed towards developing methods to prepare polymeric microcarriers under conditions that allow for controlling the average particle size, and particle size distribution, of the microcarriers. These methods include dispersion polymerization of the monomer, potentiometer dispersion of dissolved polymer within an emulsifying solution followed by solvent evaporation, electrostatically controlled extrusion, injection of dissolved polymer into an emulsifying solution through a porous membrane followed by solvent evaporation (see, for example, Kuriyama et al., *J. Appl. Poly. Sci.* 50:107 (1993); U.S. Pat. No. 4,138,383; O'Donnell et al., *J. Microencaps.* 12:155 (1995); U.S. Pat. No. 4,956,128; Amsden and Goosen, *J. Contr. Rel.* 43:183 (1997); Reyderman and Stavchansky, *Pharm. Dev. Technol.* 1:223 (1996); U.S. Pat. No. 5,376,347; and Shiga et al., *J. Pharm. Pharmacol.* 48:891 (1996).

Additional methods include vibratory excitation of a laminar jet of Monomeric material flowing in a continuous liquid medium containing a suitable suspending agent, irradiation of slowly thawing frozen monomer drops, emulsification and evaporation, emulsification and evaporation using a high shear apparatus and a high hydrophobic phase to hydrophilic phase ratio, controlled polymerization in a solvent, non-solvent mixture, extrusion into a high shear air flow, and continuous injection of dissolved polymer into a flowing non-solvent through a needle oriented in parallel to the direction of flow of the non-solvent (see also, for example, U.S. Pat. No. 4,444,961; U.S. Pat. No. 4,981,625; Sansdrap and Moes, *Int. J. Pharm.* 98:157 (1993); U.S. Pat. No. 5,643,506; Sosnowski et al., *J. Bioact. Compat. Polym.* 9:345 (1994); U.S. Pat. No. 5,260,002; and Leelarasamee et al., *J. Microencaps.* 5:147 (1988)).

As set forth below, each of these published methods has shortcomings that curtails the utility of the formed-microcarriers in various applications, and particularly when the methods are applied to the continuous production of uniformly sized microcarriers, including biocompatible, biodegradable, drug-loaded microcarriers.

Conventional monomer polymerization processes do not allow the easy inclusion of a bioactive agent or functional material within the formed polymeric microcarrier (Kuriyama et al., *J. Appl. Poly. Sci.* 50:107 (1993); U.S. Pat. No. 4,138,383; U.S. Pat. No. 4,444,961; U.S. Pat. No. 4,981,625; and Sosnowski et al., *J. Bioact. Compat. Polym.* 9:345 (1994)). For example, where the conventional methods are used to incorporate a functional compound such as a drug or other material in or on the microcarrier, the polymerization conditions may result in the deactivation of the functional compound, or the functional compound may become included in the polymer backbone.

The electrostatic extrusion process does not produce uniformly sized microcarriers of a comparatively small diameter (U.S. Pat. No. 4,956,128; Amsden and Goosen, *J. Contr. Rel.* 43:183 (1997); Reyderman and Stavchansky, *Pharm. Dev. Technol.* 1:223 (1996)).

The emulsification process of Sansdrap and Moes, *Int. J. Pharm.* 98:157 (1993), produces relatively narrow size distributions but is performed in batch mode and in a very small scale (500 milliliters).

Injecting a polymer dissolved in a volatile solvent through a porous membrane produced microcarriers of a narrow size distribution but the size of the microcarriers is controlled virtually completely by the size of the pores in the glass membrane used, and only low viscosity polymer solutions were possible (U.S. Pat. No. 5,376,347; Shiga et al., *J. Pharm. Pharmacol.* 48:891 (1996)).

The high shear emulsification process of U.S. Pat. No. 5,643,506 cannot produce a wide range of microcarriers having a narrow size distribution.

Finally, the injection method of Leelarasamee et al., *J. Microencaps.* 5:147 (1988), involves the use of a non-solvent, which requires additional, and difficult, removal steps that would decrease the incorporation efficiency of a lipophilic agent, and could not produce narrow microcarrier size distributions. Furthermore, Leelarasamee et al. does not demonstrate the ability to control the microcarrier average diameter through manipulation of the process parameters.

Thus, a need exists for a simple and reliable method for producing uniformly-sized microcarriers. Furthermore, it is desirable to be able to produce uniformly sized microcarriers in a continuous fashion in such a manner that the size of the microcarriers is easily controllable and that the process is scaleable to large production.

SUMMARY

Disclosed herein is a method of forming polymeric microcarriers for cultivating cells, comprising forming polymeric microcarriers by emulsion/aggregation from a monomer, oligomer or polymer species, and treating the polymeric microcarriers to introduce or modify a functional group for anchoring the cells on the polymeric carriers, wherein the polymeric microcarriers have an average particle diameter of from about 20 microns to about 200 microns with a particle geometric size distribution of less than about 1.35.

In embodiments, the functional group may be introduce prior to or in forming the polymeric microcarriers by emulsion/aggregation.

In further embodiments, disclosed is a vessel supporting a biologically active environment, comprising a suspension medium and polymeric microcarriers, wherein the polymeric microcarriers are emulsion/aggregation polymeric microcarriers having an average particle diameter of from about 20 microns to about 200 microns with a particle geometric size distribution of less than about 1.35, such as from about 1.00 to about 1.30 or from about 1.10 to about 1.28, and wherein the polymeric microcarriers have cultured cells thereon.

DETAILED DESCRIPTION OF THE EMBODIMENTS

Disclosed herein are processes for forming polymeric microcarriers, and polymeric microcarriers suitable for use in cell cultures. The process includes forming suitable particles (polymeric microcarriers) by emulsion/aggregation having functional groups on the surface of the particles, which enables use of the microcarriers in cell cultures. The functional groups may be introduced during the formation of the particles (polymeric microcarriers) by emulsion/aggregation, or the functional groups may be introduced to the particles (polymeric microcarriers) after the emulsion/aggregation by any suitable surface treatment.

The polymeric microcarriers disclosed herein may be utilized in cell culture techniques that have become vital to the study of cell culture, function and differentiation. Most eukaryotic cells must be attached to a surface for growth. These anchorage-dependent eukaryotic cells are used for the production of many important biological materials such as vaccines, enzymes, hormones, antibodies, interferons, and nucleic acids.

To provide a high surface-to-volume ratio, these eukaryotic cells may be cultured on small spherical particles (for example, polymeric microcarriers). Microcarriers are tiny spheres normally in the range of from about 20 microns to about 200 microns in diameter, such as from about 25 microns to about 175 microns or from about 35 microns to about 150 microns, which have a surface chemistry that allows for attachment and growth of anchorage-dependent cells in cell culture procedures.

In order for a polymeric microcarrier to be suitable for use in cell culture on all scales (for example, small cell cultures, such as test tubes, and extremely large cell cultures, such as bioreactors), the polymeric microcarrier must fulfill certain criteria.

First, the surface properties must be such that cells can adhere to the surfaces of the polymeric microcarriers with a degree of spreading, which permits cell proliferation. For homogeneous growth of the desired cells, the surface of the polymeric microcarrier must have an even, continuous contour. The surfaces of all microcarriers in the culture should have consistent properties. Thus, a microcarrier having a desired surface can provide the impetus for successful cell yields for many different lines.

Second, the particle size distribution should be narrow so that a consistent cell distribution on all polymeric microcarriers may be achieved and that confluence of the cells is achieved at approximately the same stage on each microcarrier. The cells are best cultured when microcarriers have a size of from about 20 microns to about 200 microns in diameter, such as from about 25 microns to about 175 microns or from about 35 microns to about 150 microns in diameter so that several hundred cells can be attached to each microcarrier.

Third, the density of the microcarriers should be slightly greater than that of the surrounding medium, thus facilitating easy separation of the cells and medium. The density should also be sufficiently low to allow complete suspension of the polymeric microcarriers with only gentle stirring. An optimum specific density for the polymeric microcarriers described herein is in the range of from about 1 $g/cm^3$ to about 1.2 $g/cm^3$, such as from about 1 $g/cm^3$ to about 1.15 $g/cm^3$ or from about 1.02 $g/cm^3$ to about 1.1 $g/cm^3$, which allows the polymeric microcarriers to be maintained in suspension with gentle stirring.

Fourth, the optical properties should be such that routine observation of the cells on microcarriers can be achieved using microscopy. The microcarriers should also permit use of routine cytology procedures.

And, finally, non-toxic microcarrier matrices are required not only for survival and good growth of the cells, but also when cell culture products are used for veterinary or clinical purposes.

In embodiments, the particles are comprised of emulsion/aggregation (E/A) particles, that is, particles prepared by the known emulsion/aggregation technique. Major advantages in the use of E/A particles as the polymeric microcarriers are that E/A particles have a very narrow particle size distribution, which provides more uniform movement and properties of the particles, less likelihood of agglomeration problems during use, and minimum particle size classification subsequent to formation. The E/A processes are particularly suited for making such microcarriers, as the processes are efficient in forming microcarriers of the desired size range, with narrow particle size distribution. Another advantage of E/A particles, and the polymerization processes to make such particles, is the ability to more easily incorporate additives, such as colorants (either conventional, fluorescent, or the like), magnetic and/or superparamagnetic materials, additives suitable for cell cultures, etc., into the microcarriers. The E/A processes also provide a greater degree of flexibility in forming desired microcarriers, as the E/A processes broaden the range of types of resins that can be used, and provide the ability to begin with resins that have functional groups in them or can easily be formed by reactions of the surface of the microcarrier once formed.

Emulsion/aggregation processes for making particles, for example colored particles for use in electrophotographic and other imaging processes, in which the particles are achieved via aggregation as opposed to particle size reduction, are well known. Such E/A processes generally include the steps of, for example, forming an emulsion of materials, aggregating particles to a desired size in the emulsion, coalescing the particles to a desired shape, washing and drying. For example, emulsion/aggregation processes for the preparation of toner particles are illustrated in a number of Xerox patents, the disclosures of which are totally incorporated herein by reference, such as U.S. Pat. Nos. 5,290,654, 5,278,020, 5,308,734, 5,370,963, 5,370,964, 5,344,738, 5,403,693, 5,418,108, 5,364,729, and 5,346,797. Also of interest may be U.S. Pat. Nos. 5,348,832, 5,405,728, 5,366,841, 5,496,676, 5,527,658, 5,585,215, 5,650,255, 5,650,256, 5,501,935, 6,294,606, 5,593,807, 5,853,944, 5,919,595, 6,348,561, and 5,945,245, the entire disclosures of which are also incorporated herein by reference. The E/A process is not limited in the use of certain polymers for toner particles, although polyesters and acrylic based polymers (for example, styrene acrylate) are convenient for use in the process, the use of polyesters having the further advantage of not requiring the use of any surfactants in making the particles. Fluoropolymers may also be used, these polymers showing excellent charge properties in hydrocarbons.

E/A particles herein may be made to have a suitably small size, for example from about 20 microns to about 200 microns in diameter, such as from about 25 microns to about 175 microns or from about 35 microns to about 150 microns, with an excellent particle size distribution, particularly compared to the scattered distribution typically exhibited from polymeric particles prepared by grinding techniques. The polymeric microcarriers disclosed herein have a geometric standard distribution of less than about 1.35, such as from about 1 to about 1.3 or from about 1.1 to about 1.28. In addition, E/A particles can have specific surface treatments and shapes depending on the process conditions, which can be important parameters in various end-product uses.

As used herein, the "size distribution" refers to the volume average particle size distribution index $GSD_V$ wherein the particle size distribution is measured with a suitable process such as Coulter Counter Multisizer II. The particle diameters at which a cumulative percentage of, for example, 16% are attained refer to the volume D16%, the particle diameters at which a cumulative percentage of 50% are attained are defined as volume D50%, and the particle diameters at which a cumulative percentage of 84% are attained are defined as volume D84%. The volume average particle size distribution index $GSD_V$ can be expressed by using D16%, D50%, and D84% in cumulative distribution, wherein the volume average particle size distribution index $GSD_V=(\text{volume D84\%}/\text{volume D16\%})^{1/2}$.

Specific processes for making the polymeric microcarriers disclosed herein will now be described in more detail.

In embodiments, the polymeric microcarriers may be derived from any suitable monomer, oligomer or polymer material. The specific polymer used can depend, for example, on various considerations such as compatibility with the emulsion/aggregation process, compatibility with cells to be cultured, physical properties such as strength of the particles, chemical properties such as reactivity, and the like. Each of these properties will be readily apparent, or readily determinable, by one of ordinary skill in the art. Illustrative examples of polymer resins selected for the process of generating the polymeric microcarriers disclosed herein include polyesters such as polyethylene-terephthalate, polypropylene-terephthalate, polybutylene-terephthalate, polypentylene-terephthalate, polyhexalene-terephthalate, polyheptadene-terephthalate, polyoctalene-terephthalate, polyethylene-sebacate, polypropylene sebacate, polybutylene-sebacate, polyethylene-adipate, polypropylene-adipate, polybutylene-adipate, polypentylene-adipate, polyhexalene-adipate, polyheptadene-adipate, polyoctalene-adipate, polyethylene-glutarate, polypropylene-glutarate, polybutylene-glutarate, polypentylene-glutarate, polyhexalene-glutarate, polyheptadene-glutarate, polyoctalene-glutarate polyethylene-pimelate, polypropylene-pimelate, polybutylene-pimelate, polypentylene-pimelate, polyhexalene-pimelate, polyheptadene-pimelate, poly(propoxylated bisphenol-fumarate), poly(propoxylated bisphenol-succinate), poly(propoxylated bisphenol-adipate), poly(propoxylated bisphenol-glutarate), SPAR™ (Dixie Chemicals), BECKOSOL™ (Reichhold Chemical Inc), ARAKOTE™ (Ciba-Geigy Corporation), HETRON™ (Ashland Chemical), PARAPLEX™ (Rohn & Hass), POLYLITE™ (Reichhold Chemical Inc), PLASTHALL™ (Rolmi & Hass), CYGAL™ (American Cyanamide), ARMCO™ (Armco Composites), ARPOL™ (Ashland Chemical), CELANEX™ (Celanese Eng), RYNITE™ (DuPont), STYPOL™ (Freeman Chemical Corporation) mixtures thereof and the like, polycarbonates such as LEXAN™ (G. E. Plastics), BAYLON™ (Bayer), MAKROLON™ (Mobay), MERLON™ (Mobay), PANLITE™ (Teijin Chemical), mixtures thereof and like, polyurethanes such as PELLETHANE™ (Dow), ESTANE™ (Goodyear), CYTOR™ (American Cyanamide), TEXIN™ (Mobay), VIBRATHANE™ (Uniroyal Chemical), CONATHANE™ (Conap Company), polystyrene, polyacrylate, polymethacrylate, polystyrene-butadiene, polystyrene-methacrylate, polystyrene-acrylate, mixtures thereof and the like.

Any suitable monomer, oligomer or polymer species may be used, as desired, for making the polymeric microcarrier. For example, suitable monomers that may be included in the latex emulsion from which the polymeric microcarriers are formed include functional monomers such as those described in U.S. Pat. No. 5,853,943, the entire disclosure of which is hereby incorporated by reference in its entirety. Suitable for use herein are crosslinkable monomers such as divinylbenzene and diethylene glycol methacrylate, or olefins including acrylates, acrylic acids, methacrylates, methacrylic acids, acrylonitrile, styrene and its derivatives such as methyl acrylate, ethyl acrylate, propyl acrylate, butyl acrylate, hexyl acrylate, methyl methacrylate, ethyl methacrylate, propyl methacrylate, butyl methacrylate, hexyl methacrylate, methyl styrene, acrylamide, methacrylamide, vinylpyridine, vinylpyrrolidone, vinyl-N-methylpyridinium chloride, and the like. Specific examples of nonionic monomers include styrene, alkyl substituted styrenes, halogenated styrenes, halogenated alkyl substituted styrenes and the like. It is to be understood that other useful monomers will become readily apparent to one of ordinary skill in the art based on the present disclosure.

Examples of additional useful monomers and oligomers include nonionic diolefinic or diene monomers such as butadiene, substituted butadienes, for example, methyl butadiene, isoprene, mycerine, alkyl substituted isoprene, mixtures thereof and the like. It is to be understood that other useful monomers will become readily apparent to one of ordinary skill in the art based on the present disclosure.

As desired, and based on the intended use of the polymeric microcarriers, one or more monomers, oligomers or polymers can be used in the polymerization process. When so used, the resultant resin latex can include homopolymers, copolymers, or higher order polymers (terpolymers and the like). Where copolymers or terpolymers are present, such polymers can be block, graft, random, or the like, or combinations thereof.

According to embodiments, suitable polymer materials also include functionalized polymers, for example, polymers that already incorporate functional groups, which functional groups will in turn be present and available for use in the formed polymeric microcarriers, Suitable functionalized polymers thus include, but are not limited to, polystyrene-hydroxyethyl methacrylate, polystyrene-methacrylamide, polystyrene-acrolein, polystyrene-carbohydrate, polymethylmethacrylate-N-methylolacrylamide, polystyrene-4-vinylbenzyl chloride, polystyrene-4-vinylbenzaldehyde, polystyrene-vinylbenzamine, polybutylacrylate-N-(butoxymethyl) acrylamide, polystyrene-butylacrylate-glycidylmethacrylate, mixtures thereof, and the like. Other suitable functionalized polymers will be apparent to those of ordinary skill in the art, and are equally suitable for use.

Examples of emulsion resin particles that are formed via emulsion polymerization, but before aggregation, that may be utilized to form the primary polymeric microcarriers via emulsion/aggregation include poly(styrene-alkyl acrylate), poly(styrene-1,3-diene), poly(styrene-alkyl methacrylate), poly(styrene-alkyl acrylate-acrylic acid), poly(styrene-1,3-diene-acrylic acid), poly(styrene-alkyl methacrylate-acrylic acid), poly(alkyl methacrylate-alkyl acrylate), poly(alkyl methacrylate-aryl acrylate), poly(aryl methacrylate-alkyl acrylate), poly(alkyl methacrylate-acrylic acid), poly(styrene-alkyl acrylate-acrylonitrile-acrylic acid), poly(styrene-1,3-diene-acrylonitrile-acrylic acid), and poly(alkyl acrylate-acrylonitrile-acrylic acid, poly(styrenebutadiene), poly(methylstyrene-butadiene), poly(methylmethacrylatebutadiene), poly(ethyl methacrylate-butadiene), poly(propyl methacrylate-butadiene), poly(butylmethacrylate-butadiene), poly(methylacrylate-butadiene), poly(ethyl acrylate-butadiene), poly(propyl acrylate-butadiene), poly(butyl acrylate-butadiene), poly(styrene-isoprene), poly(methylstyrene-isoprene), poly(methyl methacrylate-isoprene), poly(ethyl methacrylate-isoprene), poly(propyl methacrylate-isoprene), poly(butyl methacrylate-isoprene), poly(methylacrylate-isoprene), poly(ethyl acrylate-isoprene), poly(propyl acrylate-isoprene), and poly(butyl acrylate-isoprene); poly(styrene-propyl acrylate), poly(styrene-butyl acrylate), poly(styrene-butadiene-acrylic acid), poly(styrene-butadiene-methacrylic acid), poly(styrene-butadiene-acrylonitrile-acrylic acid), poly(styrene-butylacrylate-acrylic acid), poly(styrene-butyl acrylate-methacrylic acid), poly(styrene-butyl acrylate-acrylononitrile), and poly(styrene-butyl acrylate-acrylononitrile-acrylic acid), styrene-acrylate-carboxylic acid, poly(styrene-butadiene), poly(methyl methacrylate-butadiene), poly(ethyl methacrylate-butadiene), poly(propyl methacrylate-butadiene), poly(butyl methacrylate-butadiene), poly(methyl acrylate-butadiene), poly(ethylacrylate-butadiene), poly(propyl acrylate-butadiene), poly(butyl acrylate-butadiene), poly(styrene-isoprene), poly(methylstyrene-isoprene), poly(methyl methacrylate-isoprene), poly(ethyl methacrylate-isoprene), poly(propylmethacrylate-isoprene), poly(butyl methacrylate-isoprene), poly(methyl acrylate-isoprene), poly(ethyl acrylate-isoprene), poly(propyl acrylate-isoprene), poly(butyl acrylate-isoprene), poly(styrene-butylacrylate), poly(styrene-butadiene), poly(styrene-isoprene), poly(styrene-butyl methacrylate), poly(styrene-butyl acrylate-acrylic acid), poly(styrene-butadiene-acrylic acid), poly(styrene-isoprene-acrylic acid), poly(styrene-butyl methacrylate-acrylic acid), poly(butyl methacrylate-butyl acrylate), poly(butyl methacrylate-acrylic acid), poly(styrene-butyl acrylate-acrylonitrile-acrylic acid), poly(acrylonitrile-butyl acrylate-acrylic acid), and the like.

The resin particles suitable for use herein may be prepared by, for example, emulsion polymerization techniques, including semicontinuous emulsion polymerization methods, and the monomers utilized in such processes may be selected from, for example, styrene, acrylates, methacrylates, butadiene, isoprene, acrylonitrile; monomers comprised of an A and a B monomer wherein from about 75 to about 95 percent of A and from about 5 to about 30 percent of B is selected, wherein A can be, for example, styrene, and B can be, for example, an acrylate, methacrylate, butadiene, isoprene, or an acrylonitrile; and optionally, acid or basic olefinic monomers, such as acrylic acid, methacrylic acid, beta carboxy ethyl acrylate, acrylamide, methacrylamide, quaternary ammonium halide of dialkyl or trialkyl acrylamides or methacrylamide, vinylpyridine, vinylpyrrolidone, vinyl-N-methylpyridinium chloride and the like. The presence of acid or basic groups in the monomer or polymer resin is optional, and such groups can be present in various amounts of from about 0.1 to about 10 percent by weight of the polymer resin. Chain transfer agents, such as dodecanethiol or carbon tetrabromide, can also be selected when preparing resin particles by emulsion polymerization. Other processes of obtaining resin particles of, for example, from about 0.01 micron to about 1 micron can be selected from polymer microsuspension process, such as those illustrated in U.S. Pat. No. 3,674,736, the disclosure of which is totally incorporated herein by reference, polymer solution microsuspension process, such as disclosed in U.S. Pat. No. 5,290,654, the disclosure of which is totally incorporated herein by reference, mechanical grinding process, or other known processes; and toner processes wherein the resin possesses a crosslinking percentage of from about 1 to about 50 and/or from about 1.5 to about 30.

In embodiments, an emulsion is prepared by agitating in water a mixture of one or more of an optional nonionic surfactant such as polyethylene glycol or polyoxyethylene glycol nonyl phenyl ether, an optional anionic surfactant such as sodium dodecyl sulfonate or sodium dodecyl benzenesulfonate, and a monomer such as styrene, acrylate, methacrylate, butadiene, butylacrylate, acrylic acid, or isoprene. Oligomers and polymers may also be employed herein. Where more than one monomer is used, or particularly where a monomer or polymer species is used as a seed for the polymerization process, polymerization of the at least one monomer or polymer can take place in a manner to encapsulate or otherwise incorporate the monomer or polymer particles by heating from ambient temperature to about 80° C. Emulsion sized resin particles are produced having a volume average diameter of from about 0.02 microns to about 1.2 microns specifically including all sub-ranges and individual values within the range of about 0.02 microns to about 1.2 microns. The resulting resin emulsion, which may contain from about 20 percent to about 60 percent solids, is then diluted with water to about 15 percent solids. An additive, for example an additive as disclosed below, may be added. The optional mixture, including any optional additives, is then suitably homogenized, for example at from about 2000 to about 6000 revolution per minute, to form statically bound aggregate composite particles. The statically bound aggregate composite particles are then heated at a suitable temperature oft for example, from about 50° C. to about 105° C., such as from about 55° C. to about 100° C. or from about 45° C. to about 95° C., and for a suitable duration of time of, for example, from about 60 minutes to about 600 minutes, such as from about 100 minutes to about 550 minutes, to form polymeric particles (microcarriers) of the controlled size with narrow size distribution. As disclosed herein, the polymeric microcarriers can have a suitable diameter (average particle size) of, for example, 20 microns to about 200 microns in diameter, such as from about 25 microns to about 175 microns or from about 35 microns to about 150 microns in diameter. The polymeric microcarriers have a geometric standard distribution ($GSD_p$) of less than about 1.35, such as from about 1.0 to about 1.3 or from about 1.10 to about 1.28.

In addition to the above specifically identified monomers, oligomers and polymers, the processes disclosed wherein are also applicable to polymeric microcarriers made from polyester resins, such as sulfonated polyester resins. In these embodiments, the emulsion/aggregation process can proceed using the processes and materials as generally described in U.S. Pat. Nos. 5,348,832, 5,593,807, 5,604,706, 5,853,944, 5,919,595, and 5,945,245, the entire disclosure of which is incorporated herein by reference.

In such polyester emulsion/aggregation processes, the polyester may be obtained from the melt esterification of at least one dicarboxylic acid or diester components with at least one diol component, and optionally a sulfonated difunctional monomer, and using a polycondensation catalyst. Of course, the polyester may be formed from multiple types of one or more of the components, for example, it may be formed using more than one dicarboxylic acid or diester component, and/or more than one diol component. As used herein, "at least one" or "one or more" refers to from 1 to about 10, such as from 1 to about 8 or from 1 to about 5. The dicarboxylic acid and/or diester components are generally present in an amount of from about 42 mole percent to about 49.5 mole percent of the polyester; the diol component is generally present in an amount of about 50 mole percent of the polyester resin; and the sulfonated difunctional monomer, when present and as discussed below, is generally present in an amount of from about 0.5 to about 8 mole percent of polyester. The polycondensation catalyst is generally present in an amount of from about 0.01 to about 0.1 mole percent of the polyester. Examples of suitable dicarboxylic acid or diester components include dimethyl terephthalate and isophthalic acid; examples of suitable diol components include 1,2-propylene glycol, and propoxylated bisphenol A diethylene glycol; and examples of sulfonated difunctional monomers include dimethyl-5-sulfo-isophthalate sodium salt, and sodium 2-sulfophthalic anhydride. Suitable polycondensation catalysts include, for example, dibutyl tin oxide hydroxide.

The emulsion/aggregation process for forming such polyester polymeric microcarriers generally comprises the steps of obtaining or forming the polyester resin, followed by (a) dissipating the polyester resin in water by heating at from about 60° C. to about 120° C., which is at or near the glass transition temperature of the polyester resin (near refers to, for example, within 15° C., such as within 10° C. or within 5° C., of the glass transition temperature), with mixing for a duration of from about 1 minute to about 1 hour thereby generating suspended polyester particles of from about 0.01 micron to about 2 microns in average particle diameter; (b) subsequently adding to the resulting emulsion suspension an optional pigment or other additive dispersion, such as in an aqueous mixture containing a counterionic metal salt, and resulting in the aggregation and coalescence of resin particles and optional pigment or additive of from about 20 to about 200 microns, such as from about 25 microns to about 175 microns or from about 35 microns to about 150 microns, thereby providing polymeric microcarriers with a desired average particle diameter and (c) cooling the mixture to ambient temperature, from about 23° C. to about 27° C., washing with water from about three to about six times, and drying the product by known methods such as with a fluid bed dryer. The overall process time of the emulsion aggregation to obtain the desired particle size may be from, for example, about 6 to about 24 hours.

Although the various polyester components are not particularly limited, examples of suitable diol, diester, and the like components are set forth below. However, it will be apparent to those skilled in the art that other materials may be used.

Specific examples of the diol component suitable for use herein include ethylene glycol, 1,2-propylene glycol, 1,3-propylene glycol, 1,2-butylene glycol, 1,3-butylene glycol, 1,4-butylene glycol, 1,2-pentylene glycol, 1,3-pentylene glycol, 1,4-pentylene glycol, 1,5-pentylene glycol, 1,2-hexylene glycol, 1,3-hexylene glycol, 1,4-hexylene glycol, 1,5-hexylene glycol, 1,6-hexylene glycol, heptylene glycols, octylene glycols, decylne glycol, dodecylyne glycol, 2,2-dimethyl propane diol, propoxylated bisphenol A, ethoxylated bisphenol A, 1,4-cyclohexane diol, 1,3-cyclohexane diol, 1,2-cyclohexane diol, 1,2-cyclohexane dimethanol, 2-propene-diol, mixtures thereof, and the like. Such diols may be employed in any suitable and effective amount of, for example, from about 40 to about 60 mole percent by weight of the resin, such as from 45 to 60 mole percent or from about 45 to 55 mole percent by weight of the resin.

Specific examples of dicarboxylic acid component suitable for use herein include malonic acid, succinic acid, 2-methyl succinic acid, 2,3-dimethylsuccinic acid, dodecylsuccinic acid, glutaric acid, adipic acid, 2-methyladipic acid, pimelic acid, azeilic acid, sebacic acid, terephthalic acid, isophthalic acid, phthalic acid, 1,2-cyclohexanedioic acid, 1,3-cyclohexanedioic acid, 1,4-cyclohexanedioic acid, glutaric anhydride, succinic anhydride, dodecylsuccinic anhydride, mixtures thereof, and the like. Such dicarboxylic acids can be used in any suitable and effective amount of, for example, from about 40 to about 60 mole percent by weight of the resin, such as from 45 to 60 mole percent or from about 45 to 55 mole percent by weight of the resin.

Specific examples of dicarboxylic diesters suitable for use herein include alkyl esters, wherein the alkyl groups contain from 1 to about 23 carbons and are esters of malonate, succinate, 2-methyl succinate 2,3-dimethyl succinate, dodecyl succinate, glutarate, adipic acid, 2-methyladipate, pimelate, azeilate, sebacate acid, terephthalate, isophthalate, phthalate, 1,2-cyclohexanedioate, 1,3-cyclohexanedioate, 1,4-cyclohexanedioate, mixture thereof, and the like. Such diesters can be used in any suitable and effective amount of, for example, from about 40 to about 60 mole percent by weight of the resin, such as from 45 to 60 mole percent or from about 45 to 55 mole percent by weight of the resin.

Specific examples of sulfonated difunctional monomers suitable for use herein include the ion salts of sulfonated difunctional monomers wherein the ion is a hydrogen, ammonium, an alkali or alkaline earth such as lithium, sodium, potassium, cesium, magnesium, barium, or a metal ion such as vanadium, copper, iron cobalt, manganese, mixtures thereof and the like, and the sulfonated difunctional moiety is selected from the group including dimethyl-5-sulfo-isophthalate, dialkyl-5-sulfo-isophthalate-4-sulfo-1,8-naphthalic anhydride, 4-sulfo-phthalic acid, dimethyl 4-sulfo-phthalate, dialkyl 4-sulfo-phthalate, 4-sulfophenyl-3,5-dicarbonmethoxybenzene, 6-sulfo-2-naphthyl-3,5-dicarbomethoxybenzene, sulfo-terephthalic acid, dimethyl-sulfo-terephthalate, dialkyl-sulfo-terephthalate, sulfo-ethanediol, 2-sulfopropanediol, 2-sulfobutanediol, 3-sulfopentanediol, 2-sulfo hexanediol, 3-sulfo-2-methylpentanediol, 2-sulfo-3,3-dimethylpentanediol, sulfo-p-hydroxybenzoic acid, mixtures thereof, and the like. Such difunctional compounds can be used in an amount of, for example, from about 0.5 to about 8 mole percent by weight of the resin. In particular, dimethyl-5-sulfo-isophthalate sodium salt, and N,N-bis(2-hydroxyethyl)-2-aminoethane sulfonate available as BES from Aldrich Chemical Company, may be used.

Specific examples of polycondensation catalysts suitable for use herein include tetraalkyl titanates, dialkyltin oxide, tetraalkyltin, dialkyltin oxide hydroxide, aluminum alkoxides, alkyl zinc, dialkyl zinc, zinc oxide, stannous oxide, dibutyltin oxide, butyltin oxide hydroxide, tetraalkyl tin such as dibutyltin dilaurate, mixtures thereof, and the like. Such catalysts can be used in any suitable and effective amount of from about 0.01 mole percent to about 2 mole percent of resin, such as from about 0.01 mole percent to about 1.5 mole percent or from about 0.01 to about 1 mole percent of resin.

Specific examples of sulfonated polyesters formed from the above process include the hydrogen, ammonium, alkali or alkali earth metals such as lithium, sodium, potassium, cesium, magnesium, barium, iron, copper, vanadium, cobalt, calcium of the random copoly(ethylene-terephthalate)-copoly-(ethylene-5-sulfo-isophthalate), copoly(propylene-terephthalate)-copoly-(propylene-5-sulfo-isophthalate), copoly(diethylene-terephthalate)-copoly-(diethylene-5-sulfo-isophthalate), copoly(propylene-diethylene-terephthalate)-copoly(propylene-diethylene-5-sulfo-isophthalate), copoly(propylene-butylene-terephthalate)-copoly-(propylene-butylene-5-sulfo-isophthalate), copoly-(propoxylated bisphenol-A-fumarate)-copoly(propoxylated bisphenol A-5-sulfo-isophthalate), copoly(ethoxylated bisphenol-A-fumarate)-copoly(ethoxylated bisphenol A-5-sulfo-isophthalate), copoly(ethoxylated bisphenol-A-maleate)-copoly(ethoxylated bisphenol A-5-sulfo-isophthalate), mixtures thereof and the like, and wherein the sulfonated copoly portion is present in an amount of, for example, from about 0.5 to about 10 mole percent of the resin, such as from about 0.5 to about 9 mole percent or from about 0.5 to 8 mole percent of the resin. For the aforementioned sulfonated polyester resins, the glass transition temperature can be selected to be from about 40° C. to about 75° C., such as from about 45° C. to about 70° C. or from about 45° C. to about 65° C., as measured by the Differential Scanning Calorimeter. The number average molecular weight can be selected to be from about 2,000 grams per mole to about 150,000 grams per mole, and the weight average molecular weight can be selected to be from about 3,000 grams per mole to about 300,000 grams per mole, as each measured by the Gel Permeation Chromatograph, and the polydispersity can be selected to be from about 1.6 to about 100 as calculated by the ratio of the weight average to number average molecular weight.

The polymer resins formed from the above mentioned monomers, oligomers and polymers are generally present in the polymeric microcarriers in various effective amounts depending, for example, on the amount of the other components. Polymers in the latex resin are generally present in the polymeric microcarriers in amounts of from about 35 weight percent to about 100 weight percent of the polymeric microcarriers, such as from about 35 weight percent to about 98 weight percent or from about 40 weight percent to about 95 weight percent of the polymeric microcarriers.

One or more optional additives can be added to the resin emulsion as disclosed herein, to be incorporated into the desired polymeric particles. For example, suitable additives can include, but are not limited to, colorants, magnetic materials, superparamagnetic materials, bioactive agents, and the like.

When such additives are incorporated into the resin emulsion, optional flocculation of the emulsion can be conducted to assist in the polymeric microcarrier production. When so conducted, a flocculant such as polyaluminum chloride (PAC), polyaluminum sulfosilicate (PASS), amine, cationic salts (such as, for example, magnesium chloride, zinc acetate, calcium chloride, or the like), or cationic surfactant (such as, for example, dialkylbenzene dialkylammonium chloride) and the like is added to effect flocculation of the additives (for example, colorants, magnetic material, superparamagnetic material, bioactive agents, or the like) with the emulsion resin particles.

Examples of suitable flocculants or cationic surfactants that can be included in the processes disclosed herein include dialkyl benzenealkyl ammonium chloride, lauryl trimethyl ammonium chloride, alkylbenzyl methyl ammonium chloride, alkyl benzyl dimethyl ammonium bromide, benzalkonium chloride, cetyl pyridinium bromide, C-12, C-15, C-17 trimethyl ammonium bromides, halide salts of quaternized polyoxyethylalkylamines, dodecylbenzyl triethyl ammonium chloride, MIRAPOL ALIKAQUAT available from Alkaril Chemical Company, SANIZOL (benzalkonium chloride), available from Kao Chemicals, polyaluminum chloride (PAC), polyaluminum sulfosilicate (PASS), cationic salts (such as, for example, magnesium chloride, zinc acetate, calcium chloride, or the like), and the like, whether alone or in combination or mixture with other flocculants or cationic surfactants. Such flocculants or cationic surfactants can be included in effective amounts of, for example, from about 0.01 percent to about 10 percent by weight, such as from about 0.05 percent to about 8 percent or from about 0.5 percent to about 5 percent. The molar ratio of the cationic surfactant used for flocculation to the anionic surfactant used in the latex preparation may be in the range of from about 0.5 to 4. It is to be understood that other useful cationic surfactants will become readily apparent to one of ordinary skill in the art based on the present disclosure.

As mentioned above, magnetic and/or superparamagnetic materials can also be incorporated into the polymeric microcarriers. Such magnetic materials can be included, for example, to give the polymeric microcarriers magnetic and/or superparamagnetic properties, for colorant properties, or the like. Suitable magnetic and/or superparamagnetic materials that can be used herein include magnetites, ferrites, and the like. Examples of suitable magnetites, in addition to the magnetites mentioned above, include a mixture of iron oxides ($FeO$, $Fe_2O_3$), including those commercially available as MAPICO BLACK™. Other examples of suitable magnetic materials include barium ferrite powder ($BaO.6Fe_2O_3$), strontium ferrite powder ($SrO.6Fe_2O_3$), barium-strontium ferrite powder ($Ba_xSr_{1-x}O.6Fe_2O_3$), $SmCo_5$-based powder, $Sm_2Co_{17}$-based powder, $Nd_2Fe_{14}B$-based powder, $Sm_2Fe_{17}N_3$-based powder, $(NdDy)_{15}Fe_{79}B_6$, alloys of 33Ne 66Fe 1B, an Nd—Fe—B-based quenched magnetic powder (such as the product MQP-B manufactured by GM), ferrite particles, and the like. Examples of suitable ferrites include ferrites such as MnZn ferrite and NiZn ferrite. Any other suitable magnetic and/or superparamagnetic material can also be used. The magnetic and/or superparamagnetic material can be present in the polymeric microcarriers in any of various effective amounts, for example, in amounts of from about 10 percent by weight to about 75 percent by weight of the polymeric microcarriers, such as from about 20 percent to about 65 percent or from about 30 percent to about 55 percent by weight of the polymeric microcarriers.

Examples of useful chain transfer agents that can be incorporated into the polymeric microcarriers include dodecanethiol, carbon tetrabromide and the like, which can be used to control the molecular weight properties of the polymer when emulsion polymerization is carried out. It is to be understood that other useful chain transfer agents will become readily apparent to one of ordinary skill in the art based on the present disclosure. An effective concentration of a chain transfer agent that is generally employed may be from about 0.005 to about 10 (percent by weight, such as from about 0.01 to about 5 percent by weight or from about 0.1 to about 3 percent by weight of the reaction mixture.

Examples of useful optional free radical initiators that can be incorporated into the polymeric microcarriers include azo-type initiators such as 2-2'-azobis(dimethyl-valeronitrile), azobis(isobutyronitrile), azobis(cyclohexane-nitrite), azobis (methyl-butyronitrile), mixtures thereof, and the like, peroxide initiators such as benzoyl peroxide, lauroyl peroxide, methyl ethyl ketone peroxide, isopropyl peroxy-carbonate, 2,5-dienethyl-2,5-bas(2-ethylhexanoyl-peroxy)hexane, di-tert-butyl peroxide, cumene hydroperoxide, dichlorobenzoyl peroxide, potassium persulfate, ammonium persulfate, sodium bisulfate, combination of potassium persulfate, sodium bisulfate and the like, and mixtures thereof. It is to be understood that other useful free radical initiators will become readily apparent to one of ordinary skill in the art based on the present disclosure. An effective quantity of an initiator is generally within the range of from about 0.1 percent to about 15 percent by weight of the reaction mixture, such as from 0.1 percent to about 10 percent by weight or from about 0.1 percent to about 8 percent by weight of the reaction mixture.

If desired for the particular applications of the polymeric microcarriers, the polymeric microcarriers may also optionally include known charge additives in effective suitable amounts of from 0.01 to 10 weight percent, such as from about 0.05 to about 8 weight percent or from about 0.1 to about 5 weight percent. Such charge additives are well known for use in electrostatographic imaging toner compositions. Examples of such charge additives include alkyl pyridinium halides, bisulfates, the charge control additives of U.S. Pat. Nos. 3,944,493; 4,007,293; 4,079,014; 4,394,430 and 4,560,635, which illustrate a toner with a distearyl dimethyl ammonium methyl sulfate charge additive, the entire disclosures of which are totally incorporated herein by reference, as well as negative charge enhancing additives such as aluminum complexes, and the like.

An additive such as one or more colorants, for instance pigments or dyes, can be added to the resin emulsion in an amount less than or equal to about 65 percent by weight of the particle solids, such as from about 0.5 percent to about 65 percent by weight of particle solids. The colorants may be pretreated so as to bind the resin particles disclosed herein. Alternatively, the colorants may be encapsulated by the resin particles in whole or in part. The resulting mixture may optionally be dispersed utilizing a Brinkman or IKA homogenizer.

In general, useful colorants or pigments include carbon black, magnetite, or mixtures thereof; cyan, yellow, magenta, or mixtures thereof; or red, green, blue, brown, or mixtures thereof. Typical useful colorants or pigments are present in an effective amount of from about 1 to about 65 percent by weight such from about 1 to about 25 percent by weight or from about 3 to about 10 percent by weight. Furthermore, in embodiments, it may be possible to utilize lesser amounts of the colorants, such as in the range of from about 0.1 to about 10 percent by weight or from about 0.5 to about 5 percent by weight. Specific useful colorants include Paliogen Violet 5100 and 5890 (BASF), Normandy Magenta RD-2400 (Paul Uhlich), Permanent Violet VT2645 (Paul Uhlich), Heliogen Green L8730 (BASF); Argyle Green XP-111-S (Paul Uhlich), Brilliant Green Toner GR 0991 (Paul Uhlich), Lithol Scarlet D3700 (BASF), Toluidine Red (Aldrich), Scarlet for Thermoplast NSD Red (Aldrich), Lithol Rubine Toner (Paul Uhlich), Lithol Scarlet 4440, NBD 3700 (BASF), Bon Red C (Dominion Color), Royal Brilliant Red RD-8192 (Paul Uhlich), Oracet Pink RF (Ciba Geigy), Paliogen Red 3340 and 3871K (BASF), Lithol Fast Scarlet L4300 (BASF), Heliogen Blue D6840, D7080, K7090, K6910 and L7020 (BASF), Sudan Blue OS (BASF), Neopen Blue FF4012 (BASF), PV Fast Blue B2G01 (American Hoechst), Irgalite Blue BCA (Ciba Geigy), Paliogen Blue 6470 (BASF), Sudan II, III and IV (Matheson, Coleman, Bell), Sudan Orange (Aldrich), Sudan Orange 220 (BASF), Paliogen Orange 3040 (BASF), Ortho Orange OR 2673 (Paul Uhlich), Paliogen Yellow 152 and 1560 (BASF). Lithol Fast Yellow 0991K (BASF), Paliotol Yellow 1840 (BASF), Novaperm Yellow FGL (Hoechst), Permanent Yellow YE 0305 (Paul Uhlich), Lumogen Yellow D0790 (BASF), Suco-Gelb L1250 (BASF), Suco-Yellow D1355 (BASF), Sico Fast Yellow D1165, D1355 and D1351 (BASF), Hostaperm Pink E (Hoechst), Fanal Pink D4830 (BASF), Cinquasia Magenta (DuPont), Paliogen Black L0084 (BASF), Pigment Black K801 (BASF) and carbon blacks such as REGAL 330 (Cabot), Carbon Black 5250 and 5750 (Columbian Chemicals), and the like or mixtures thereof.

Additional useful colorants include pigments in water based dispersions such as those commercially available from Sun Chemical, for example SUNSPERSE BHD 6011X (Blue 15 Type), SUNSPERSE BHD 9312X (Pigment Blue 15 74160), SUNSPERSE BHD 6000X (Pigment Blue 15:3 74160), SUNSPERSE GHD 9600X and GHD 6004X (Pigment Green 7 74260), SUNSPERSE QHD 6040X (Pigment Red 122 73915), SUNSPERSE RHD 9668X (Pigment Red 185 12516), SUNSPERSE RHD 9365X and 9504X (Pigment Red 57 15850:1, SUNSPERSE YHD 6005X (Pigment Yellow 83 21108), FLEXIVERSE YFD 4249 (Pigment Yellow 17 21105), SUNSPERSE YHD 6020X and 6045X (Pigment Yellow 74 11741), SUNSPERSE YHD 6001X and 9604X (Pigment Yellow 14 21095), FLEXIVERSE LFD 4343 and LFD 9736 (Pigment Black 7 77226) and the like or mixtures thereof. Other useful water based colorant dispersions commercially available from Clariant include HOSTAFINE Yellow GR, HOSTAFINE Black T and Black TS, HOSTAFINE Blue B2G, HOSTAFINE Rubine 17613 and magenta dry pigment such as Toner Magenta 6BVP2213 and Toner Magenta E02 which can be dispersed in water and/or surfactant prior to use.

Other useful colorants include magnetites, such as Mobay magnetites M08029, M08060; Columbian magnetites; MAPICO BLACKS and surface treated magnetites; Pfizer magnetites CB4799, CB5300, CB5600, MCX6369; Bayer magnetites, BAYFERROX 8600, 8610; Northern Pigments magnetites, NP-604, NP-608; Magnox magnetites TMB-100, or TMB-104; and the like or mixtures thereof. Specific additional examples of pigments include phthalocyanine HELIOGEN BLUE L6900, D6840, D7080, D7020, PYLAM OIL BLUE, PYLAM OIL YELLOW, PIGMENT BLUE 1 available from Paul Uhlich & Company, Inc., PIGMENT VIOLET 1, PIGMENT RED 48, LEMON CHROME YELLOW DCC 1026, E.D. TOLUIDINE RED and BON RED C available from Dominion Color Corporation, Ltd., Toronto, Ontario, NOVAPERM YELLOW FGL, HOSTAPERM PINK E from Hoechst, and CINQUASIA MAGENTA available from E.I. DuPont de Nemours & Company, and the like. Examples of magentas include, for example, 2,9-dienethyl-substituted quinacridone and anthraquinone dye identified in the Color Index as CI 60710, CI Dispersed Red 15, diazo dye identified in the Color Index as CI 26050, CI Solvent Red 19, and the like or mixtures thereof. Illustrative examples of cyans include copper tetra(octadecyl sulfonamido) phthalocyanine, x-copper phthalocyanine pigment listed in the Color Index as C174160, CI Pigment Blue, and Anthrathrene Blue, identified in the Color Index as CI 69810, Special Blue X-2137, and the like or mixtures thereof; while illustrative examples of yellows that may be selected are diarylide yellow 3,3-dichlorobenzidene acetoacetanilides, a monoazo pigment identified in the Color Index as CI 12700, CI Solvent Yellow 16, a nitrophenyl amine sulfonamide identified in the Color Index as Foron Yellow SE/GLN, CI Dispersed Yellow 33 2,5-dienethoxy-4-sulfonanilide phenylazo-4'-chloro-2,5-dienethoxy acetoacetanilide, and Permanent Yellow FGL. Colored magnetites, such as mixtures of MAPICO BLACK and cyan components may also be selected as pigments with the process disclosed herein. Colorants include pigment, dye, mixtures of pigment and dye, mixtures of pigments, mixtures of dyes, and the like. It is to be understood that other useful colorants will become readily apparent to one of skill in the art based on the present disclosure.

Dyes that are invisible to the naked eye but detectable when exposed to radiation outside the visible wavelength range (such as ultraviolet or infrared radiation), such as dansyl-lysine, N-(2-aminoethyl)-4-amino-3,6-disulfo-1,8-dinaphthalimide dipotassium salt, N-(2-aminopentyl)-4-amino-3,6-disulfo-1,8-dinaphthalimide dipotassium salt, Cascade Blue ethylenediamine trisodium salt (available from Molecular Proes, Inc.), Cascade Blue cadaverine trisodium salt (available from Molecular Proes, Inc.), bisdiazinyl derivatives of 4,4'-diaminostilbene-2,2'-disulfonic acid, amide derivatives of 4,4'-diaminostilbene-2,2'-disulfonic acid, phenylurea derivatives of 4,4'-disubstituted stilbene-2,2'-disulfonic acid, mono- or di-naphthyltriazole derivatives of 4,4'-disubstituted stilbene disulfonic acid, derivatives of benzthiazole, derivatives of benzoxazole, derivatives of benzimidazole, derivatives of coumarine, derivatives of pyrazolines containing sulfonic acid groups, 4,4'-bis(triazin-2-ylamino)stilbene-2,2'-disulfonic acids, 2-(stilben-4-yl)naphthotriazoles, 2-(4-phenylstilben-4-yl)benzoxazoles, 4,4-bis(triazo-2-yl)stilbene-2,2'-disulfonic acids, 1,4-bis(styryl)biphenyls, 1,3-diphenyl-2-pyrazolines, bis(benzazol-2-yl)derivatives, 3-phenyl-7-(triazin-2-yl)coumarins, carbostyrils, naphthalimides, 3,7-diaminodibenzothiophen-2,8-disulfonic acid-5,5-dioxide, other commercially available materials, such as C.I. Fluorescent Brightener No. 28 (C.I. 40622), the fluorescent series Leucophor B-302, BMB (C.I. 290), BCR, BS, and the like (available from Leucophor), and the like, are also suitable for use as a colorant.

In addition, suitable colorants that can be used herein include one or more fluorescent colorants, which can be pigments, dyes, or a mixture of pigments and dyes. For example, suitable fluorescent pigment concentrates are disclosed in, for example, U.S. Pat. No. 4,911,830, the entire disclosure of which is incorporated herein by reference, and suitable fluorescent colorants are disclosed in, for example, U.S. Pat. Nos. 4,243,694 and 5,554,480, the entire disclosures of which are incorporated herein by reference. Suitable inorganic fluorescent pigments can be prepared, for example, by adding trace amounts of activating agents such as copper, silver and manganese to high purity sulfides of heavy metals or alkaline earth metals such as zinc sulfide, which are used as raw materials, and calcining them at a high temperature. Suitable organic fluorescent pigments can be prepared, for example, by dissolving fluorescent dyes in the vehicles of synthetic resins or ones prepared by dyeing the dispersed matters of fine resin particles obtained by emulsion polymerization or suspension polymerization with fluorescent dyes. The synthetic resins can include, but are not limited to, vinyl chloride resins, alkid resins and acrylic resins, and the fluorescent dyes include, but are not limited to, C.I. acid yellow 7, C.I. basic red 1 and the like.

Although not limited thereto, suitable fluorescent dyes include, but are not limited to, those belonging to the dye families known as rhodamines, fluoresciens, coumarins, napthalimides, benzoxanthenes, acridines, azos, and the like. Suitable fluorescent dyes include, for example, Basic Yellow 40, Basic Red 1, Basic Violet 11, Basic Violet 10, Basic Violet 16, Acid Yellow 73, Acid Yellow 184, Acid Red 50, Acid Red 52, Solvent Yellow 44, Solvent Yellow 131, Solvent Yellow 85, Solvent Yellow 135, Solvent Yellow 43, Solvent Yellow 160 and Fluorescent Brightner 61. Suitable fluorescent pigments include, but are not limited to, those available from Day-Glo Color Corp. of Cleveland, Ohio, such as aurora pink T-11 and GT-11, neon red T-12, rocket red T-13 or GT-13, fire orange T-14 or GT-14N, blaze orange T-15 or GT-15N, arc yellow T-16, saturn yellow T-17N, corona magenta GT-21 and GT-17N, and the like.

Examples of a surfactant, which may optionally be added to the aggregates before coalescence is initiated, can be anionic surfactants, such as sodium dodecylbenzene sulfonate, sodium dodecylnaphthalene sulfate, dialkyl benzenealkyl, sulfates and sulfonates, abitic acid, available from Aldrich, NEOGEN R, NEOGEN SC obtained from Kao, BIOSOFT D-40 obtained from Stepan, and the like or mixtures thereof. They can also be selected from nonionic surfactants such as polyvinyl alcohol, polyacrylic acid, methalose, methyl cellulose, ethyl cellulose, propyl cellulose, hydroxy ethyl cellulose, carboxy methyl cellulose, polyoxyethylene cetyl ether, polyoxyethylene lauryl ether, polyoxyethylene octyl ether, polyoxyethylene octylphenyl ether, polyoxyethylene oleyl ether, polyoxyethylene sorbitan monolaurate, polyoxyethylene stearyl ether, polyoxyethylenenonylphenyl ether, dialkylphenoxypoly(ethyleneoxy)ethanol, available from Rhone-Poulenac as IGEPAL CA-210, IGEPAL CA-520, IGEPAL CA-720, IGEPAL CO-890, IGEPAL CO-720, IGEPAL CO-290, IGEPAL CA-210, ANTAROX 890, ANTAROX 897, and the like or mixtures thereof. An effective amount of the anionic or nonionic surfactant utilized in the coalescence to primarily stabilize the aggregate size against further growth with temperature is from about 0.01 to about 10 percent by weight, such as from about 0.05 to about 8 percent or from about 0.5 to about 5 percent by weight of the reaction mixture. Additional methods of stabilizing aggregate size include raising the pH of the emulsion above 6, such as through the addition of sodium hydroxide or potassium hydroxide.

Once the polymeric microcarriers are formed, they can be isolated from the reaction mixture by any suitable means. Suitable isolation methods include, but are not limited to, filtration, particle classification, and the like.

Alternatively, the formed polymeric microcarriers may optionally be washed and dried by conventional means. For example, the formed polymeric microcarriers can be washed using water, such as deionized water, or other suitable materials. The formed polymeric microcarriers may likewise be dried using, for example, a heated drying oven or the like.

The formed polymeric microcarriers have a diameter of from about 20 microns to about 200 microns in diameter such as from about 25 microns to about 175 microns or from about 35 microns to about 150 microns in diameter. The polymeric microcarriers have a geometric standard distribution (GSD) of less than about 1.35, such as from about 1 to about 1.3 or from about 1.1 to about 1.28. The particle shape factor of the spherical polymeric microcarrier may be from about 0.95 to about 1, such as from about 0.96 to about 1 or from about 0.97 to about 0.995, as analyzed for particle circularity using a Sysmex FPIA instrument (and wherein a value of 1 represents a perfect sphere). The surface area of the polymeric microcarrier may be from about 0.01 $m^2/g$ to about 0.8 $m^2/g$, such as from about 0.03 $m^2/g$ to about 0.7 $m^2/g$ or from about 0.05 $m^2/g$ to about 0.5 $m^2/g$, as determined by the Brunauer, Emmett and Teller (BET) method.

Following any washing and/or drying, the polymeric particles may be subjected to an optional chemical surface treatment. For example, the polymeric particles may be subjected to any desirable surface treatment to alter the chemical and/or physical properties of the particle, such as hydrophobicity, hydrophilicity, surface charge, and the like, or to attach or alter functional groups present on the surface of the microcarriers.

Most polymers are hydrophobic in nature and commercially available. If hydrophobic polymers are desired, then such polymers do not need to be treated except to alter a different property. However, hydrophobic polymers may be subjected to surface treatment to alter any physical and/or chemical properties of the polymer. Examples of hydrophobic polymers include polyolefins such as low density polyethylene, polypropylene, high density polyethylene, ultra high molecular weight polyethylene, blends of polyolefins with other polymers or rubbers; polyethers, such as polyoxmethylene; polyamides, such as poly(hexamethylene adipamide); halogenated polymers, such as polyvinylidenefluoride, polytetra-fluoroethylene, fluorinated ethylene-propylene copolymer, and polyvinyl chloride; aromatic polymers, such as polystyrene; ketone polymers such as polyetheretherketone; methacrylate polymers, such as polymethylmethacrylate; polyesters, such as polyethylene terephthalate; and copolymers, such as ADS, ethylene propylene diene mixture.

Simple oxidative treatments such flame treatment, corona discharge, or chemical oxidation may generally lead to an increase in surface hydrophilicity. Bonding ability may also increase as a result of the occurrence of oxygenated groups such as carboxyl, hydroxyl and carbonyl on the modified polymer surfaces.

Typically, a method of increasing the hydrophilicity of the polymer surface may be in a three step process comprising: (1) producing carboxyl, carbonyl and hydroxyl groups on the polymer surface by an oxidation treatment process such as etching with oxidizing acid solutions, corona discharge, flame treatment or plasma treatment; (2) reacting the groups on the oxidized polymer surface with a compound belonging to groups A and B, wherein group A includes heterocyclic compounds having three or four ring atoms, such as oxiranes, thiiranes, aziridines, azetidinones, oxetanes, and group B includes carbodiimides and isocyanates; and (3) post-treating the polymer material previously treated according to step (2) with further application of compounds containing nucleophilic groups, such as alcohols, water, amines, carboxylic acids and hydroxycarboxylic acids that react with the modified surface either by opening aziridine rings, or react with the residual isocyanate groups. The reaction according to step (2) may be carried out in aprotic organic solvents, such as ketones and ethers, due to the fact that the compounds in groups A and B are typically not stable in aqueous solution.

Polymeric materials may also be surface modified to provide optimal surface charge for sufficient wetting and adhesion strength. In general, polymers have a low surface charge when compared to other common materials such as metals and woods. The lower the surface charges of the adherent, the more difficult the wetting of the adhesive. Thus, polymer surfaces may often be subjected to treatments in an attempt to increase surface charge. Physical surface treatments such as the corona discharge process and plasma treatment are commonly used treatments within the polymer industry to alter polymer surface charge.

The corona discharge process requires an instrument to provide a high voltage spark. An air gap located between the machine and a part therein is filled with high voltage. This high voltage field contains accelerating free electrons, which ionize the air gap. This extremely reactive gas contains free electrons, positive ions, UV rays, and other polar entities. These species act to charge the polymer surface by breaking bonds and creating free radicals that may then form oxygen functional groups along the polymer surface. The functional groups and free radicals also work to increase the surface charge of the polymer. The corona discharge process is conducted at atmospheric pressure.

Plasma treatment is similar to the corona discharge process in that a plasma, or an ionized gas, is used to charge the polymer surface by oxidation. The plasma, or ionized gas, used in plasma treatment consists of an equal mixture of positive and negative charges. The main difference in plasma treatment when compared to the corona discharge process is that the process is performed at a pressure less than atmospheric. The plasma operation is higher in energy than the corona discharge process. Creating a vacuum to treat the polymer is expensive, but offers a repeatable process because the atmosphere is controlled.

The formed polymeric microcarriers may also or alternatively be surface halogenated, partially or wholly, for example up to 100 percent, such as from about 10 percent to about 95 percent or from about 20 percent to about 80 percent, to convert olefinic double bonds by an electrophilic addition reaction in the surface polymer chain backbone and pendant groups into the corresponding halogenated hydrocarbon functionality. In many instances, surface halogenation of the polymeric microcarriers affords further control of the variety of rheological properties that may be obtained from the copolymer resins. Surface halogenation is accomplished with a gaseous mixture or liquid solution of an effective amount of from about 0.01 to about 10, such as from about 0.01 to about 7 or from about 0.01 to about 5, double bond molar equivalents of halogen gas or halogen liquid dissolved in water, or an organic solvent, for example, chlorine gas, liquid bromine, or crystalline iodine dissolved in a solvent, such as an aliphatic alcohol, like ethanol which does not dissolve or substantially alter the size or shape of the polymeric microcarriers.

When more reactive halogens such as fluorine are used, an inert carrier gas, such as argon or nitrogen, may be selected as a diluent, for example, from about 0.1 to about 98 percent by volume of the inert gas relative to the reactive halogen gas, to moderate the extent of reaction, and the temperature and control corrosivity of the halogenation-encapsulation process.

A number of equally useful halogenating agents are known that afford equivalent reaction products with olefinic double bonds as disclosed by, for example, House in "Modern Synthetic Reactions", W. A. Benjamin, Inc., $2^{nd}$ Ed., Chapter 8, page 422, and references cited therein, the disclosure of which is incorporated in its entirety by reference.

The aforementioned halogenation can be considered an addition reaction. That is, for example, the halogen reacts with, and diffuses into, the polymer resin, whereby a shell thereof is formed. The shell can be of various effective thicknesses; generally, however, the shell is of a thickness of from about 1 micron or less, and more specifically from about 0.01 to about 1 micron or from about 0.1 to about 1 micron, in embodiments. Typical amounts of halogen consumed include, for example, from about 0.1 to about 1 grain of halogen per 100 grams of polymer resin.

Numerous other functional groups can be present on the surface of the polymeric microcarriers, either by virtue of them being present in the polymer material itself resulting from the polymerization process, or by means of surface modification of the formed microcarriers.

The functional group may be introduced into the composition initially when generating the latex emulsion or as a surface treatment of the formed polymeric microcarriers. The functional groups found on the surface of the formed polymeric microcarriers may be achieved as a result of the selected starting materials. Various methods for forming such surface functional groups are known in the art, and will be apparent based on the present disclosure. A majority of the functional group(s) will be found on the surface of the polymeric microcarriers. However, a portion of the functional group(s) may migrate towards the center of the polymeric microcarriers. One of ordinary skill in the art will readily recognize that such a migration is dependent on the functional group and the composition of the polymeric microcarriers and the suspension medium.

The emulsion may be made to include monomers that result in the presence of functional groups on the surface of the particles formed, and/or further chemical treatment of the microcarriers may be performed to create functional groups on the surface. The functional groups may enable the covalent bonding or complexation of, glass, collagen (gelatin), recombinant proteins, carbohydrates, haptens and the like, for enhancing animal cell attachment.

In embodiments, the polymeric microcarriers may be derived from monomers, oligomers or polymers that result in the presence of functional groups on the surface of the formed polymeric microcarriers, and/or further chemical treatment of the polymeric microcarriers may be performed to create such functional groups on the surface.

Such functional groups may enable the covalent bonding or complexation of radioactive materials, biological materials, or ligands for attaching radioactive or biological materials. Suitable monomers, oligomers and polymers, and surface treatment materials that provide appropriate functional groups are discussed herein.

Post-copolymerization of functional monomers, oligomers or polymers with residual double bonds of the polymeric microcarriers containing divinylbenzene or diethylene glycol methacrylate may also be used for grafting functional groups to the polymeric microcarriers, provided the grafted monomer is copolymerized with styrene or acrylate-like units. The functional groups grafted on the surface can be —C—O—, —C=O, —O—C=O, —C—O—O, —C—N, —C=N, —C≡N, —NH, —NH$_2$, —CF, —CF$_2$, —CF$_3$, or —SO$_3$. These double bonds may be at least partially reacted, for example undergoing cationic polymerization during chloromethylation by chloromethylether in the presence of Friedel-Crafts catalysts. "Partially reacted" refers to the double bonds of the function monomers, oligomers or polymers being reacted during any suitable polymerization reaction up to 100 percent, such as from 10 percent to about 95 percent or from about 20 percent to about 85 percent.

Other surface treatments or modifications suitable for use herein include such modification and treatments as disclosed in U.S. Pat. Nos. 5,869,16, 5,902,710, 6,143,457, the entire disclosures of which are incorporated herein by reference.

Of course, two or more different surface treatments or modifications can be performed on the same microcarrier, if desired. Such multiple surface treatments or modifications can be advantageous for example, to enable attachment of multiple different materials or to provide multiple functionalities to the microcarriers.

The polymeric microcarriers prepared according to the processes disclosed herein may be employed in a variety of uses. While not being limited to any particular uses, the microcarriers are especially useful for cell culture functions. Accordingly, the polymeric microcarriers disclosed herein, including any additives incorporated therein or thereon, may be compatible with the desired cells.

In embodiments, the polymeric microcarriers disclosed herein are utilized in culturing cells in bioreactor systems. Such bioreactor systems have many advantages over roller bottles and other flat-surface formats for the large-scale cultivation of anchorage-dependent cells. These advantages include lower total costs, ease of harvesting and downstream processing procedures, quality assurance and process control, ease of scale-up, an overall reduction in the space required for a given-sized operation, higher titers, ability to precisely control cell growth condition in sophisticated, computer-controlled bioreactors, and a significant reduction in technician labor costs.

As used herein "bioreactor systems" refer to, for example, any device or system that supports a biologically active environment. A bioreactor thus may refer to a device or system meant to grow cells or tissues in the context of cell culture, as discussed herein.

As explained above, the polymeric microcarriers disclosed herein may be used when growing cells, for example, eukaryotic cells, in a synthetic environment. Culture conditions, such as growth media, pH, temperature, etc., vary for each type of cell to be cultured. One skilled in the art will understand how to manipulate such culture conditions for the specific type of cell to be cultured. For example, medium suitable for culturing cells may include nutrients, antibiotics, amino acids, vitamins, salts, sugars, buffers, fatty acids and lipids, proteins and peptides, and any mixture thereof. Examples of amino acids may include alanine, arginine, asparagine, aspartic acid, cystine, glutamic acid, glutamine, glycine, histidine, hydroxyproline, isoleucine, leucine, lysine, methionine, 3-methylhistidine, ornithine, phenylalanine, proline, serine, taurine, threonine, trytophan, tyrosine, and valine. Examples of vitamins may include thiamin, riboflavin, niacin, vitamin B6, folic acid, vitamin B12, biotin, pantothenic acid, choline, para-amin-obenzoic acid, and inositol. Examples of sugars may include glucose, galactose, maltose and fructose. Examples of salts may include NaCl, KCl, KH$_2$PO$_4$, CaCl$_2$ (anhydrous), MgSO$_4$ (anhydrous), NaH$_2$PO$_4$.H$_2$O and Na$_2$FHPO$_4$ (anhydrous). Examples of buffers include sodium bicarbonate, HEPES zwitterionic (N-Cyclohexyl-2-aminoethanesulfonic acid), and Tris(Hydroxymethyl) aminomethane. Examples of fatty acids and lipids include cholesterols and steroids. Examples of proteins and peptides may include albumin, transferrin, fibronectin and fetuin.

Specifically, an example of a medium suitable for culturing mammalian cells includes glucose, penicillin, streptomycin, whole serum, amino acids, such as arginine, cystine, glutamine, histidine, isoleucine, leucine, lysine, methionine, phenylalanine, threonine, tryptophan, tyrosine and valine, vitamins such as biotin, choline, folate, nicotinamide, pantothenate, pyridozal, thiamine and riboflavin, and salts such as NaCl, KCl, NaH$_2$PO$_4$, NaHCO$_3$, CaCl$_2$ and MgCl$_2$. One skilled in the art is able to formulate compositions specific to the cultivation of a particular cell.

In addition to the medium having nutrients necessary for the cultivation of the desired cells, the polymeric microcarriers themselves may also include nutrients necessary for such cultivation. As with the suspension medium, suitable nutrients are dependent upon the type of cells being cultured.

Specific examples of cells that may be cultured using the polymeric microcarriers, as disclosed herein, include eukaryotic cells such as chick embryo fibroblasts (CEF) cells, mouse capillary endothelial cells, fetal rat pancreas cells, human lymphoblastoid cells, human cervical carcinoma cells, human glioma cells (HeLa), human embryo fibroblasts (MRC-5) cells, human kidney cells (Flow 4000/Clone 2), Chinese hamster ovary cells (CHO), human foreskin fibroblasts (FS-4) cells, pig kidney cells, dog kidney cells, mouse cortex tumor adrenal cells, human amnion cells, human amniotic cells, human bone marrow cells, human oral carcinoma cells, human conjunctiva cells, rabbit cornea cells, human coronary endothelium cells, human monocytic leukemia cells, human primary hepatocytes liver cells, Chinese hamster lung cells, human lymphoblastoid cells, rat peritoneal macrophage cells, human melanoma cells, chicken myoblasts muscle cells, pig thymoid cells, and the like.

It will be appreciated that various of the above-disclosed and other features and functions, or alternatives thereof, may be desirably combined into many other different systems or applications. Also, various presently unforeseen or unanticipated alternatives, modifications, variations or improvements therein may be subsequently made by those skilled in the art, and are also intended to be encompassed by the following claims.

EXAMPLE

The narrow particle size distribution polymeric microcarrier composition are prepared by emulsion aggregation via controlled aggregation of styrene-acrylate-carboxylic acid functional polymer latexes. The process is initially performed by mixing functional latex in water and adding a metal halide coagulant, such as polyaluminum chloride (PAC) followed by heating. When the aggregates approach the required size (that is, from about 35 to about 150 microns in diameter), growth is hindered through adjustment of the pH (for example, the pH is adjusted to be from about 4 to about 9, such as from about 5 to about 6.5) with a known caustic agent (such as sodium hydroxide). The slurry of desired sized aggregates is then heated above the glass transition temperature (Tg) of the resin (typically above about 80° C., such as above about 90° C.), followed by lowering the pH to about 1.5 to about 6 (more particularly the pH was lowered from about 2.5 to about 5.5) with an acid to coalesce aggregates into discrete polymer particles. Once the polymeric particles are the desired shape (such as spherical), the particle slurry is cooled to an appropriate working temperature, such as from about 10° C. to about 50° C., or about 30° C. After the emulsion aggregation process, the polymeric particles are washed with water to remove residual surfactants and impurities, and dried.

Polymeric particles having a 42 micron narrow size distribution were prepared by the emulsion process with styrene-acrylate-carboxylic acid functional polymer latexes, as described above. Specifically, a styrene-acrylate-carboxylic acid functional polymer latex comprised of a styrene/n-butyl acrylate/β-carboxyethyl acrylate copolymer of 74:20:6 weight percentage was prepared with 0.5 pph (part per hundred) dodecanethiol (chain transfer agent), and 1.5 weight percent of ammonium persulfate initiator was synthesized by a semicontinuous emulsion polymerization process using the anionic surfactant DOWFAX. 2A1™ (sodium tetrapropyl diphenoxide disulfonate, 47 percent active, available from Dow Chemical). The GSD of the formed polymeric microcarriers was about 1.27, as determined by the Layson Cell particle analyzer; and the formed polymeric microcarriers possessed a specific density of about 1.04 g/cm$^3$.

The formed polymeric microcarriers were suspended in a medium and were covered with HVT infected chick embryo fibroblasts (CEF) cells. The medium was C3978 TiterHigh™ Chick Embryo Fibroblast Basal Medium available from Sigma-Aldrich Co., which contains inorganic salts, bicarbonate buffer, essential and non-essential amino acids, vitamins, other organic compounds, and trace elements. The CEF cells were successfully cultured and formed a confluent mass on the formed polymeric microcarriers. Living CEF cells were then harvested from the polymeric microcarriers using a dilute solution of T4174 Trypsin-EDTA solution available from Sigma Co. Product Description: Enzyme Commission (EC) Number: 3.4.21.4, Molecular Weight: 23.4 kDa1.

A very high percentage of the harvested cells were viable. In particular, the percentage of viable cell was from about 75% to about 83%.

It will be appreciated that various of the above-disclosed and other features and functions, or alternatives therof, may be desirably combined into many other different systems or applications. Also, various presently unforseen or unanticipated alternatives, modifications, variations or improvements therein may be subsequently made by those skilled in the art, and are also intended to be encompassed by the following claims.

What is claimed is:

1. A method of forming polymeric microcarriers for cultivating cells, comprising:

forming polymeric microcarriers by emulsion/aggregation from a monomer, oligomer or polymer species, wherein the forming by emulsion/aggregation comprises:

a) forming a polymeric resin from the monomer, oligomer or polymer species;

b) aggregating the polymeric resin into larger polymeric particles;

c) coalescing the polymeric particles into the polymeric microcarriers;

d) treating the polymeric microcarriers to introduce or modify a functional group for anchoring the cells on the polymeric microcarriers, wherein the polymeric microcarriers have a particle diameter of from 35 microns to about 200 microns, a particle geometric size distribution of about 1.35 or less, and a particle shape factor of from about 0.950 to about 1; and e) optionally isolating the polymeric microcarriers.

2. The method according to claim 1, wherein the functional group is capable of binding proteins, carbohydrates and/or haptens.

3. The method according to claim 1, wherein the polymeric microcarriers have a specific density of from about 1 g/cm$^3$ to about 1.2 g/cm$^3$.

4. The method according to claim 1, wherein the polymeric microcarriers are formed from the monomer, oligomer or polymer species and an additive.

5. The method according to claim 4, wherein the additive is a colorant, a fluorescent material, a magnetic material and/or a supermagnetic material.

6. The method according to claim 1, wherein the average particle diameter is from 35 microns to about 150 microns.

7. The method according to claim 1, wherein the polymeric microcarriers have a surface area of from about 0.01 m$^2$/g to about 0.8 m$^2$/g.

8. The method according to claim 1, wherein the functional group is —C—O—, —C═O, —O—C═O, —C—O—O, —C—N, —C═N, —C≡N, —NH, —$NH_2$, —CF, —$CF_2$, —$CF_3$ or —$SO_3$.

9. A method of forming polymeric microcarriers for cultivating cells, comprising:

i) forming polymeric microcarriers by emulsion/aggregation from a monomer, oligomer or polymer species; and ii) treating the polymeric microcarriers to introduce or modify a functional group for anchoring the cells on the polymeric microcarriers, wherein the forming by emulsion/aggregation comprises:

a) providing a polyester resin formed from the monomer, oligomer or polymer species;

b) dispersing the polyester resin in an aqueous medium optionally comprising a surfactant, to provide a suspension of suspended particles of the polyester resin;

c) homogenizing the suspension;

d) aggregating and coalescing the homogenized suspension by adding a cationic metal salt and optional additives;

e) heating the aggregates, to form the polymeric microcarriers, wherein the polymeric microcarriers have a particle diameter of from 35 microns to about 200 microns, a particle geometric size distribution of about 1.35 or less, and a particle shape factor of from about 0.950 to about 1; and f) optionally isolating the polymeric microcarriers.

10. The method according to claim 9, wherein the heating is conducted at or near a glass transition temperature of the polyester resin.

11. A method of forming polymeric microcarriers for cultivating cells, comprising:
   i) providing a monomer, oligomer or polymer species having a functional group; and
   ii) forming polymeric microcarriers by emulsion/aggregation to derive a microcarrier with the functional group thereon from the monomer, oligomer or polymer species having the functional group, wherein the forming by emulsion/aggregation comprises:
   a) forming a polymeric resin from the monomer, oligomer or polymer species having the functional group;
   b) aggregating the polymeric resin into larger polymeric particles;
   c) coalescing the polymeric particles into the polymeric microcarriers, wherein the functional group is capable of anchoring the cells and the polymeric microcarriers have an average particle diameter of from 35 microns to about 200 microns and a particle geometric size distribution of about 1.35 or less; and
   d) optionally isolating the polymeric microcarriers.

12. A vessel comprising a suspension medium and polymeric microcarriers, wherein the polymeric microcarriers are the emulsion/aggregation polymeric microcarriers of claim 1, and wherein the polymeric microcarriers comprise cultured cells anchored to the functional groups of the polymeric microcarriers.

13. The vessel according to claim 12, wherein the vessel is a bioreactor.

14. The vessel according to claim 12, wherein the cells are eukaryotic cells.

15. The vessel according to claim 12, wherein the functional groups bind proteins, carbohydrates and/or haptens.

16. The vessel according to claim 12, wherein the functional groups include —C—O—, —C=O, —O—C=O, —C—O—O, —C—N, —C=N, —C≡N, —NH, —NH$_2$, —CF, —CF$_2$, —CF$_3$ or —SO$_3$.

17. The vessel according to claim 12, wherein the polymeric microcarriers have a specific density of from about 1 g/cm$^3$ to about 1.2 g/cm$^3$.

18. The vessel according to claim 12, wherein the average particle diameter is from 35 microns to about 150 microns.

19. The vessel according to claim 12, wherein the polymeric microcarriers are suspended in the suspension medium.

20. The vessel according to claim 12, wherein the suspension medium comprises antibiotics, amino acids, vitamins and/or salts.

21. The vessel according to claim 12, wherein the polymeric microcarriers have a surface area of from about 0.01 m$^2$/g to about 0.8 m$^2$/g.

22. The method according to claim 1, wherein the polymeric microcarriers are polyester.

* * * * *